US006346501B1

(12) United States Patent
Herzog et al.

(10) Patent No.: US 6,346,501 B1
(45) Date of Patent: Feb. 12, 2002

(54) CATALYST BASED ON PALLADIUM, CADMIUM, ALKALI AND LANTHANOIDS AND A METHOD FOR PRODUCING VINYL ACETATE

(75) Inventors: Bernhard Herzog, Oberhausen (DE); Tao Wang; Ioan Nicolau, both of Corpus Christi, TX (US)

(73) Assignees: Celanese Chemicals Europe GmbH, Frankfurt (DE); Celanese International Corporation, Dallas, TX (US)

( * ) Notice: Subject to any disclaimer, the term of this patent is extended or adjusted under 35 U.S.C. 154(b) by 0 days.

(21) Appl. No.: 09/581,462
(22) PCT Filed: Dec. 2, 1998
(86) PCT No.: PCT/EP98/07817
  § 371 Date: Jul. 20, 2000
  § 102(e) Date: Jul. 20, 2000
(87) PCT Pub. No.: WO99/29419
  PCT Pub. Date: Jun. 17, 1999

(30) Foreign Application Priority Data

Dec. 11, 1997 (DE) .......................................... 197 55 022

(51) Int. Cl.$^7$ ............................ B01J 23/60; C07C 67/05
(52) U.S. Cl. ...................... 502/304; 502/302; 502/326; 502/330; 502/339; 502/340; 502/560; 502/245
(58) Field of Search ................................ 502/304, 302, 502/326, 330, 339, 340; 560/245

(56) References Cited

U.S. PATENT DOCUMENTS

| 5,935,897 A | * | 8/1999 | Trubenbach et al. |
| 5,935,898 A | * | 8/1999 | Trubenbach et al. |
| 5,990,344 A | * | 11/1999 | Couves et al. |
| 6,225,496 B1 | * | 5/2001 | Baker et al. |

FOREIGN PATENT DOCUMENTS

| EP | 0634214 | 1/1995 |
| WO | 9637455 | 11/1996 |

* cited by examiner

Primary Examiner—Gary Geist
Assistant Examiner—Robert W. Deemie
(74) Attorney, Agent, or Firm—Bierman, Muserlian and Lucas

(57) ABSTRACT

The invention relates to a catalyst which contains palladium and/or compounds thereof, cadmium compounds, alkali metal compounds and at least one lanthanoid metal. The invention also relates to the utilization of the catalyst in order to produce vinyl acetate from acetic acid, ethylene and oxygen or gases containing oxygen.

12 Claims, No Drawings

CATALYST BASED ON PALLADIUM, CADMIUM, ALKALI AND LANTHANOIDS AND A METHOD FOR PRODUCING VINYL ACETATE

This application is a 371 of PCT/EP98/07817 filed Dec. 2, 1998.

The present invention relates to a catalyst which comprises palladium and/or its compounds, cadmium compounds, alkali metal compounds and at least one lanthanoid metal compound, and to its use for preparing vinyl acetate from acetic acid, ethylene and oxygen or oxygen-containing gases.

It is known that ethylene can be reacted with acetic acid and oxygen or oxygen-containing gases in the gas phase on palladium/cadmium/alkali metal-containing fixed bed catalysts to give vinyl acetate. According to U.S. Pat. No. 4,902,823, U.S. Pat. No. 3,939,199, U.S. Pat. No. 4,668,819, the catalytically active metal salts are applied to the catalyst carrier by impregnation, spraying on, vapor deposition, immersion or precipitation. The preparation of a palladium, cadmium and potassium-containing catalyst is also known, entailing a carrier material which has been provided with a binder, for example an alkali metal or alkaline earth metal carboxylate, being washed before the impregnation with an acid and being treated after the impregnation with a base (EP-A-0 519 435).

EP-A-0 634 209 discloses the preparation of palladium, cadmium and potassium-containing catalysts by the carrier particles being impregnated by being intimately mixed with a solution of palladium, cadmium and potassium salts and then being immediately dried, the dynamic viscosity of the solution being at least 0.003 Pa·s and the solution volume for the impregnation being 5 to 80% of the pore volume of the carrier particles. EP-A-0 634 208 discloses the possibility of using a solution volume which is more than 80% of the pore volume of the carrier particles for the impregnation. However, with this procedure it is necessary to select a time before starting the drying which is so short that, after the end of the drying, a shell of 5 to 80% of the pore volume comprises said metal salts.

Palladium, cadmium and potassium-containing catalysts can also be prepared by the process disclosed in EP-A-0 634 214 by spraying the carrier particles while being intimately mixed with a solution of palladium, cadmium and potassium salts in the form of drops with an average diameter of at least 0.3 mm or in the form of liquid jets, and then immediately drying them, the dynamic viscosity of the solution being at least 0.003 Pa·s, and the solution volume in the spraying being 5 to 80% of the pore volume of the carrier particles.

The PCT application WO 96/37455 discloses that catalysts of this type can be considerably improved by adding at least one rhenium and/or at least one zirconium compound. Thus, a palladium, cadmium, potassium-containing shell catalyst shows a space-time yield (gram of vinyl acetate formed per liter of catalyst and hour) of 922 (g/l·h), whereas an initial productivity of 950 g/l·h is observed after addition of zirconium under conditions which are otherwise the same.

It has now been found, surprisingly, that palladium, cadmium and potassium-containing catalysts can be distinctly improved by adding at least one lanthanoid metal compound, i.e. they afford a higher space-time yield with identical or greater selectivity for vinyl acetate.

The invention accordingly relates firstly to a process for preparing vinyl acetate in the gas phase from ethylene, acetic acid and oxygen or oxygen-containing gases on a catalyst which comprises palladium and/or its compounds, cadmium compounds and alkali metal compounds on a carrier, wherein the catalyst additionally comprises at least one lanthanoid metal compound.

The invention relates secondly to a catalyst which comprises palladium and/or its compounds, cadmium compounds and alkali metal compounds on a carrier, wherein the catalyst additionally comprises at least one lanthanoid metal compound.

The term "lanthanoid metals" means the 14 rare earth elements cerium, praseodymium, neodymium, promethium, samarium, europium, gadolinium, terbium, dysprosium, holmium, erbium, thulium, ytterbium and lutetium, and the elements scandium, yttrium and lanthanum because their chemical behavior resembles that of the rare earth elements.

Suitable carriers are the known inert carrier materials such as silica, alumina, aluminosilicates, silicates, titanium oxide, zirconium oxide, titanates, silicon carbide and carbon. Particularly suitable carriers of this type are those with a specific surface area of 40 to 350 $m^2/g$ (measured by the BET method) and an average pore radius of 50 to 2000 Å (Angstrom) (measured by mercury porosimetry), especially silica ($SiO_2$) and $SiO_2/Al_2O_3$ mixtures. These carriers can be used in any form such as, for example, in the form of beads, tablets, rings, stars or particles of other shapes, with a diameter or length and thickness generally of 3 to 9 mm.

Carriers of these types can be prepared, for example, from aerogenic $SiO_2$ or an aerogenic $SiO_2/Al_2O_3$ mixture which can be prepared, for example, by flash hydrolysis of silicon tetrachloride or a silicon tetrachloride/aluminum trichloride mixture in an oxyhydrogen flame (U.S. Pat. No. 3,939,199).

Suitable solvents for the palladium, cadmium, alkali metal and lanthanoid metal salts are all compounds in which the selected salts are soluble and which can easily be removed again after the impregnation by drying. Suitable for the acetates, if they are used, are in particular, unsubstituted carboxylic acids having 2 to 10 carbon atoms such as acetic acid, propionic acid, n- and iso-butyric acid and the various valeric acids. Among the carboxylic acids, acetic acid is preferred because of its physical properties and for economic reasons. Water is particularly suitable for the chlorides and chloro and acetato complexes. Additional use of another solvent is expedient if the salts are insufficiently soluble in acetic acid or in water. Thus, for example, palladium chloride can be dissolved considerably better in an aqueous acetic acid than in glacial acetic acid. Suitable additional solvents are those which are inert and are miscible with acetic acid or water. Those which may be mentioned as additions for acetic acid are ketones such as acetone and acetylacetone, also ethers such as tetrahydrofuran or dioxane, but also hydrocarbons such as benzene.

It is possible to apply a plurality of salts of palladium, cadmium, alkali metal and the particular lanthanoid metal, but generally exactly one salt of each of these elements is applied.

It is possible to prepare either so-called "fully impregnated" catalysts where the catalytically active metal compounds have penetrated into the carrier particles as far as the core, or else so-called "shell catalysts" where the metal salts have advanced only into an outer part, of variable size, of the carrier particles, i.e. the so-called "shell" of the particles, and not as far as the core.

The elements palladium, cadmium, alkali metal and lanthanoid metal to be applied in each case can be applied in the form of salt solutions singly or else in any suitable combination in any suitable sequence, preferably using a single solution which contains these elements to be applied in the form of salts. It is particularly preferred to use a single solution which contains exactly one salt of each of these elements to be applied. This solution may moreover contain a mixture of salts of at least two different lanthanoid metals, but this solution preferably contains one salt of only one lanthanoid metal.

Where the following speaks generally of "the solution of the salts", the same applies analogously to the case where a plurality of solutions are employed in sequence, each of which contains only part of the totality of salts to be applied, in which case the total of the individual parts amounts to the total quantity of salts to be applied to the carrier.

The procedure for preparing fully impregnated catalysts is preferably as follows (U.S. Pat. No. 4,902,823, U.S. Pat. No. 3,393,199, U.S. Pat. No. 4,668,819):

The catalyst carrier is impregnated with the solution of the active components in such a way that the carrier material is covered with the solution and, where appropriate, excess solution is then poured off or filtered. It is advantageous, with regard to losses of solution, to employ only the amount of solution corresponding to the integral pore volume of the catalyst carrier, and to mix this amount carefully so that the particles of the carrier material are uniformly wetted. It is expedient to carry out the impregnation step and the mixing simultaneously, for example in a rotating drum or a tumble drier, in which case the drying can follow immediately. It is further generally expedient for the composition of the solution used for impregnating the catalyst carrier to be such that the required quantity of active substances is applied by single impregnation. However, this quantity can also be applied by a plurality of impregnations, in which case each impregnation is preferably followed by drying.

The procedure for preparing shell catalysts is preferably by one of the following three methods, always using a solution of at least one salt of at least one of the elements palladium, cadmium, alkali metal and lanthanoid metal with a dynamic viscosity of at least 0.003 Pa·s, preferably 0.005 to 0.009 Pa·s:

1. The carrier particles are sprayed one or more times while being intimately mixed with the solution of the salts in the form of drops with an average diameter of at least 0.3 mm or in the form of liquid jets and, after each spraying, immediately dried. "Immediate" drying means in this connection that drying of the sprayed particles must be started without delay. It is generally sufficient for drying of the particles to be started no later than 30 minutes after the end of a spraying. The solution volume for a spraying is 5 to 80% of the pore volume of the carrier particles. This method is described in detail in EP-A-0 634 214, which is incorporated herein by reference.
2. The carrier particles are impregnated one or more times while being intimately mixed with the solution and are dried immediately after each impregnation. "Immediate" drying means in this connection the same as for the first method, and the solution volume for each impregnation is 5 to 80% of the pore volume of the carrier particles.

This method is described in detail in EP-A-0 634 209, which is likewise incorporated herein by reference.
3. The carrier particles are impregnated with the solution one or more times and dried after each impregnation but, differing from the 2nd method, the solution volume has no upper limit. It is now more than 80% of the pore volume for each impregnation. Because the solution volume is larger, intimate mixing is not absolutely necessary although generally beneficial. Instead, it is now necessary for the duration of each impregnation and the time before the subsequent drying starts, i.e. the time from the start of each impregnation to the start of the subsequent drying, to be so short that, after the end of the last drying, a shell of 5 to 80% of the pore volume of the carrier particles contains the catalytically active elements. The duration of this short time which must be chosen for this purpose can easily be determined by preliminary tests. This method is described in detail in EP-A-0 634 208, which is incorporated herein by reference.

Drying of the impregnated or sprayed catalyst carrier is preferably carried out under reduced pressure (0.01 to 0.08 MPa) both for fully impregnated catalysts and for shell catalysts. The temperature during the drying ought generally to be 50 to 80° C., preferably 50 to 70° C. It is further generally recommended to carry out the drying in a stream of inert gas, for example in a stream of nitrogen or carbon dioxide. The residual solvent content after the drying ought preferably to be less than 8% by weight, in particular less than 6% by weight.

The finished palladium, cadmium, alkali metal and at least one lanthanoid metal-containing catalysts have the following metal contents:

| Palladium content: | generally | 0.6–3.5% by weight, |
|---|---|---|
| | preferably | 0.8–3.0% by weight, |
| | in particular | 1.0–2.5% by weight |
| Cadmium content: | generally | 0.1–2.5% by weight, |
| | preferably | 0.4–2.5% by weight, |
| | in particular | 1.3–2% by weight |
| Alkali metal content: | generally | 0.3–10% by weight, |
| Potassium is preferably used. | | |
| Potassium content: | generally | 0.5–4.0% by weight, |
| | preferably | 1.0–3.0% by weight, |
| | in particular | 1.5–2.5% by weight |
| Lanthanoid metal content: | generally | 0.01–1% by weight |
| | preferably | 0.05–0.5% by weight, |
| | in particular | 0.2–0.5% by weight. |

If more than one lanthanoid metal is used to dope the palladium, cadmium and alkali metal-containing catalysts, the term "lanthanoid metal content" means the total content of all the lanthanoid metals present in the finished catalyst. The stated percentages always relate to the amounts of the elements palladium, cadmium, alkali metal and lanthanoid metal present in the catalyst, based on the total weight of catalyst (active elements plus anions plus carrier material).

Suitable salts are all salts of palladium, cadmium, an alkali metal and a lanthanoid element which are soluble; the acetates, the chlorides, and the acetato and chloro complexes are preferred. However, in the case of interfering anions such as, for example, in the case of chlorides, it must be ensured that these anions are substantially removed before use of the catalyst. This takes place by washing the doped carrier, for example with water after the metals have been converted into an insoluble form, for example by reduction and/or by reaction with compounds having an alkaline reaction.

Particularly suitable salts of palladium are the carboxylates, preferably the salts of aliphatic monocarboxylic acids having 2 to 5 carbon atoms, for example the acetate, propionate or butyrate. Further suitable examples are the nitrate, nitrite, oxide hydrate, oxalate, acetylacetonate or acetoacetate. Because of its good solubility and availability, the particularly preferred palladium salt is palladium acetate.

Particularly suitable as cadmium compound is the acetate.

The alkali metal compound preferably employed is at least one sodium, potassium, rubidium or caesium compound, in particular at least one potassium compound.

Particularly suitable compounds are carboxylates, in particular acetates and propionates. Compounds which are converted under the reaction conditions into the alkali metal acetate, such as, for example, the hydroxide, the oxide or the carbonate, are also suitable.

Particularly suitable as lanthanoid metal compound are the chlorides, nitrates, acetates and acetylacetonates.

If a reduction of the palladium compounds is carried out, which is sometimes beneficial, a gaseous reducing agent can be used for this purpose. Examples of suitable reducing agents are hydrogen, methanol, formaldehyde, ethylene, propylene, isobutylene, butylene or other olefins. The reduction temperature is generally between 40 and 260° C., preferably between 70 and 200° C.

It is generally expedient to use a reducing agent which is diluted with inert gas and contains 0.01 to 50% by volume, preferably 0.5 to 20% by volume, of reducing agent for the reduction. Nitrogen, carbon dioxide or a noble gas, for example, is suitable as inert gas. The reduction can also be carried out in liquid phase at a temperature from 0° C. to 90° C., preferably from 15 to 25° C. Examples of reducing agents which can be used are aqueous solutions of hydrazine, formic acid or alkali metal borohydrides, in particular sodium borohydride. The amount of the reducing agent depends on the amount of palladium; the reduction equivalent should be at least equal to the oxidation equivalent in quantity, but larger amounts of reducing agent are not harmful. The reduction is carried out after the drying.

Vinyl acetate is generally prepared by passing acetic acid, ethylene and oxygen-containing gases at temperatures from 100 to 220° C., preferably 120 to 200° C., under pressures from 0.1 to 2.5 MPa, preferably 0.1 to 2.0 MPa, over the finished catalyst, it being possible to circulate unreacted components. It is also advantageous in some circumstances to dilute with inert gases such as nitrogen or carbon dioxide. Carbon dioxide is particularly suitable for the dilution because it is formed in small amounts during the reaction.

With the same reaction conditions it is possible with the aid of the novel catalysts to prepare more vinyl acetate per reactor volume and time with, at the same time, improved selectivity by comparison with known catalysts. This facilitates the workup of the resulting crude vinyl acetate because the vinyl acetate content in the gas discharged from the reactor is higher, which further results in a saving of energy in the workup part. A suitable workup is described, for example, in U.S. Pat. No. 5,066,365.

If, on the other hand, it is wished to keep the space-time yield constant, it is possible to reduce the reaction temperature and thus carry out the reaction more selectively, with the same total productivity, in which case there is a saving of precursors. This is also associated with a decrease in the amount of carbon dioxide, which is formed as by-product and therefore must be removed, and in the loss of entrained ethylene which is associated with this removal. In addition, this procedure results in an increase in the useful life of the catalyst.

The following examples are intended to illustrate the invention but do not restrict it. The percentages of the elements palladium, cadmium, potassium and of the lanthanoid metal are percentages by weight based on the total weight of the catalyst.

SiO$_2$ was used as catalyst carrier material, from which tablets with a diameter and a height each of 6 mm were produced as disclosed in DE-A 3 912 504. These tablets were used as catalyst carrier. The pore volume of 1 l of carrier was 392 ml.

EXAMPLE 1

At 65° C., 25.3 g (0.11 mol) of palladium acetate, 25 g (0.09 mol) of cadmium acetate, 25.3 g (0.26 mol) of potassium acetate and 6.82 g (0.016 mol) of cerium acetylacetonate were dissolved in 130 ml of glacial acetic acid (solution volume=33% of the pore volume), and the highly viscous solution was introduced into a receiver preheated to 65° C. 1 l of catalyst carrier was likewise heated to 65° C. and placed in a flask. All the impregnation solution was poured over the carrier particles and intimately mixed until the entire impregnation solution had been absorbed by the catalyst carrier. This step was complete after 3 minutes. Drying took place in a stream of nitrogen at 65° C. and 0.02 MPa to constant weight. The finished catalyst contained 2.0% by weight Pd, 1.7% by weight Cd, 1.7% by weight K and 0.38% by weight Ce.

COMPARATIVE EXAMPLE 1a

The procedure was as in Example 1, but no lanthanoid metal salts were added to the impregnation solution containing palladium acetate, cadmium acetate and potassium acetate. The finished catalyst contained 2.0% by weight Pd, 1.7% by weight Cd and 1.7% by weight K.

The method used for testing the novel catalyst prepared as in Example 1 and the catalyst prepared as in Comparative Example 1a was as follows. 225 ml of the particular catalyst were introduced into a reaction tube with an internal diameter of 20 mm and a length of 65 cm. Then the gas to be reacted was passed over the catalyst under a pressure of 0.8 MPa (reactor inlet) and at a catalyst temperature of 150° C. for 5 days. This gas consisted of 58% by volume ethylene, 25% by volume nitrogen, 12% by volume acetic acid and 5% by volume oxygen; the results are evident from the table.

| Example | Space-time yield | $CO_2$ selectivity |
| --- | --- | --- |
| 1 | 820 | 7.0 |
| Comparative Example 1a | 720 | 7.6 |

Space-time yield in grams of vinyl acetate per liter of catalyst and hour.

$CO_2$ selectivity in % based on the amount of ethylene reacted.

It was found, surprisingly, that even small additions of lanthanoid metal compounds to the known palladium, cadmium and potassium-containing catalysts distinctly improve the $CO_2$ selectivity and the productivity (space-time yield) of these catalysts for preparing vinyl acetate.

What is claimed is:

1. A catalyst comprising a cadmium compound, an alkali metal compound and palladium or a compound thereof on a carrier and additionally at least one lanthanoid compound.

2. A catalyst of claim 1 containing at least one potassium compound.

3. A catalyst of claim 1 wherein the amount of lanthanoid compound is 0.01 to 1% by weight calculated as lanthanoid metal.

4. A catalyst of claim 3 wherein the amount of lanthanoid compound is 0.05 to 0.5% by weight calculated as lanthanoid metal.

5. A catalyst of claim 1 comprising 0.1 to 2.5% by weight of a cadmium compound calculated as cadmium metal, 0.3 to 10% by weight of an alkali metal compound calculated as alkali metal, 0.6 to 3.5% by weight of palladium or palladium compound calculated as palladium metal and 0.01 to 1% by weight of a lanthanoid compound calculated as lanthanoid metal on carrier particles.

6. A catalyst of claim 5 wherein the lanthanoid metal is cerium.

7. In a process for the preparation of vinyl acetate by the vapor phase reaction of ethylene, acetic acid and oxygen or an oxygen containing gas in the presence of a catalyst, the improvement comprising using as the catalyst, the catalyst of claim 1.

8. The process of claim 7 wherein the catalyst contains at least one potassium compound.

9. The process of claim 7 wherein the catalyst contains 0.01 to 1.0% by weight of lanthanoid compound calculated as lanthanoid metal.

10. The process of claim 9 wherein the amount of lanthanoid compound is 0.05 to 0.5% by weight calculated as lanthanoid metal.

11. In a process for the preparation of vinyl acetate by the vapor phase reaction of ethylene, acetic acid and oxygen or an oxygen containing gas in the presence of a catalyst, the improvement comprising using as the catalyst, the catalyst of claim 5.

12. The process of claim 11 wherein the lanthanoid metal is cerium.

* * * * *